US005538501A

United States Patent [19]
Caswell

[11] Patent Number: 5,538,501
[45] Date of Patent: Jul. 23, 1996

[54] WRIST SUPPORT

[75] Inventor: Charles A. Caswell, Altus, Okla.

[73] Assignee: OK-1 Manufacturing Company, Altus, Okla.

[21] Appl. No.: 308,004

[22] Filed: Sep. 16, 1994

[51] Int. Cl.$^6$ .................................................. A61F 5/00
[52] U.S. Cl. .................................. 602/64; 602/21; 2/16; 2/161.4; 2/162; 128/878; 128/879
[58] Field of Search ................................ 2/16–21, 161.4, 2/162, 163; 602/20, 21, 62, 60, 64, 69; 128/878, 879

[56] References Cited

U.S. PATENT DOCUMENTS

| | | |
|---|---|---|
| D. 320,872 | 10/1991 | McCrane . |
| 3,533,407 | 10/1970 | Smith ......................................... 602/64 |
| 3,815,908 | 6/1974 | Hashimoto ............................ 602/64 X |
| 3,848,874 | 11/1974 | Elkins, Jr. .............................. 602/64 X |
| 4,084,586 | 4/1978 | Hettick ................................... 602/64 X |
| 4,843,651 | 7/1989 | Gramza et al. ............................... 2/162 |
| 4,854,309 | 8/1989 | Elsey ..................................... 602/64 X |
| 4,958,384 | 9/1990 | McCrane . |
| 5,100,314 | 11/1992 | Peters ..................................... 602/64 X |
| 5,376,006 | 12/1994 | Phillips et al. ......................... 602/64 X |
| 5,397,296 | 3/1995 | Sydor et al. ............................ 602/64 X |
| 5,413,553 | 5/1995 | Downes ................................. 602/64 X |
| 5,415,624 | 5/1995 | Williams ............................... 602/64 X |

FOREIGN PATENT DOCUMENTS 162610  11/1985  European Pat. Off. ................. 602/64

*Primary Examiner*—Richard J. Apley
*Assistant Examiner*—Kim M. Lee
*Attorney, Agent, or Firm*—Dunlap & Codding

[57] ABSTRACT

An improved wrist support for protection against development of carpal tunnel syndrome. The support includes a body member having an upper portion and a lower portion, the lower portion having variable stretch sections for providing variable amounts of support along the wrist, hand and arm. The upper portion of the body member encircles a portion of the thumb for added support. The upper portion of the body member is constructed of neoprene for support, impact resistance and comfort. The fingers of the hand are left substantially unencumbered when the wrist support is in place about the wrist.

3 Claims, 4 Drawing Sheets

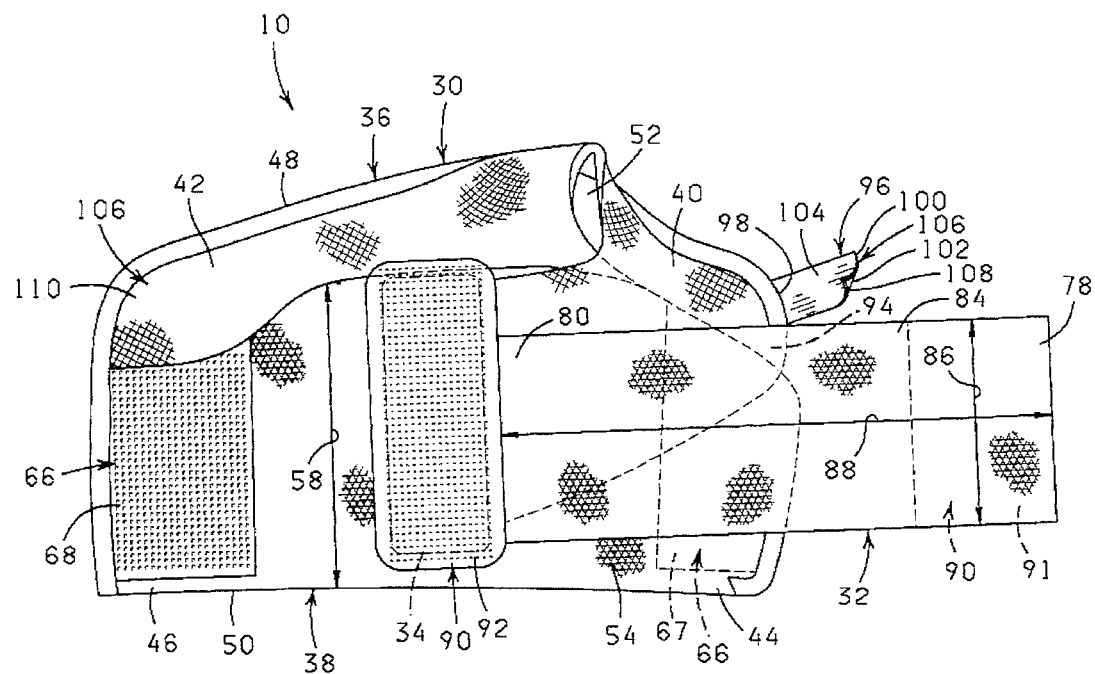
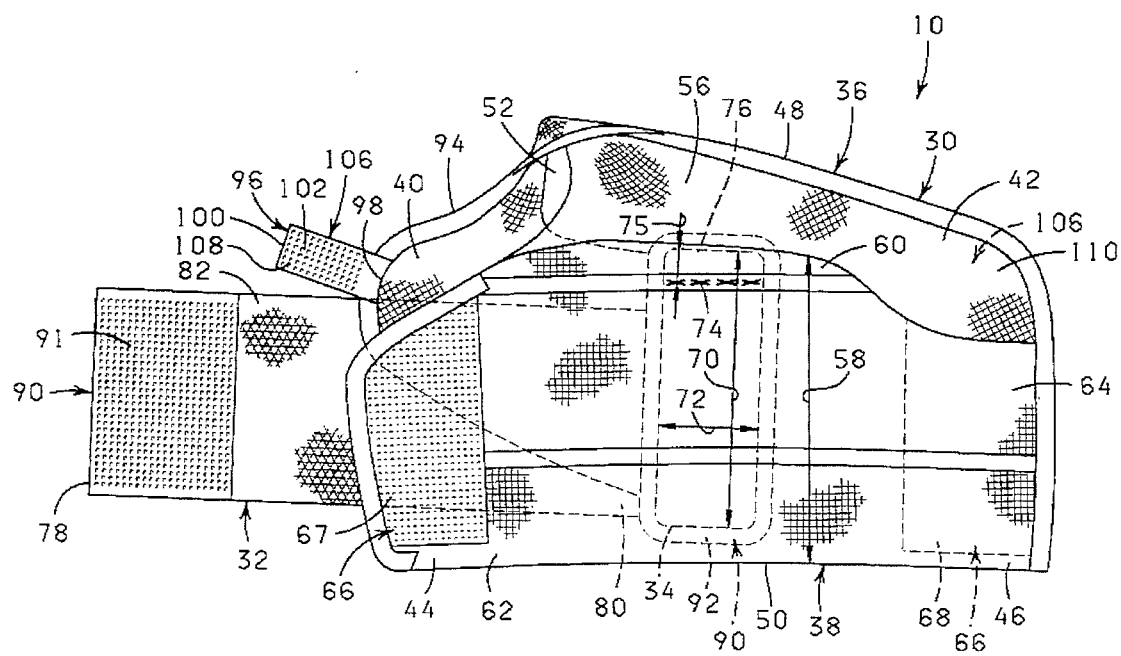
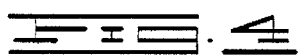

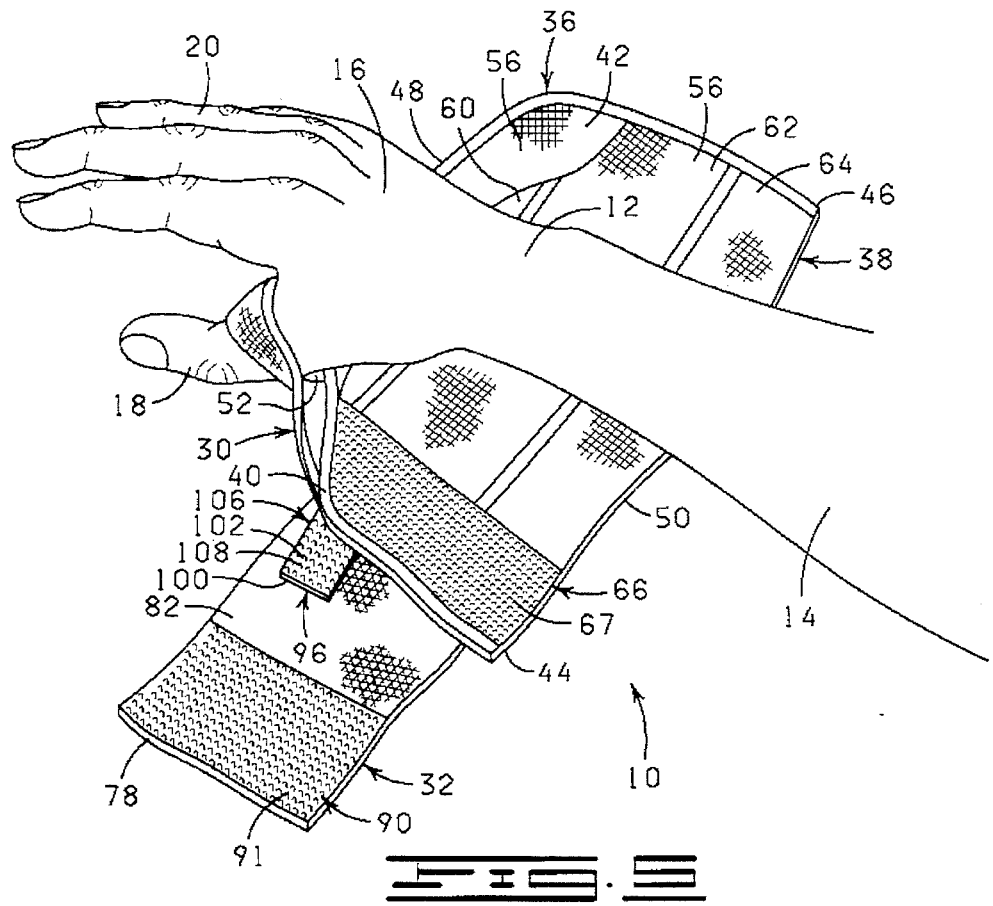
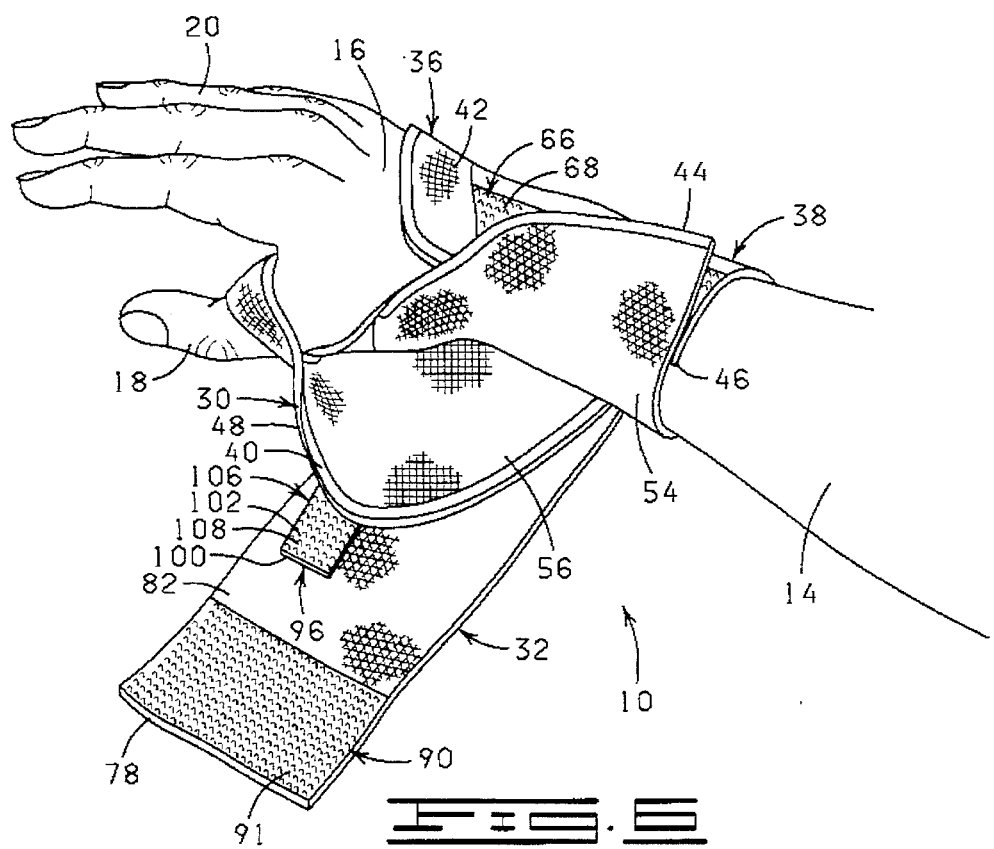

WRIST SUPPORT

FIELD OF THE INVENTION

The present invention relates generally to wrist supports and, more particularly, but not by way of limitation, to an improved wrist support for preventing the wearer of the support from developing carpal tunnel syndrome.

BACKGROUND OF THE INVENTION

Carpal tunnel syndrome is a medical condition in which pain, numbness or a tingling sensation is felt in the area of the wrist, thumb and fingers. Carpal tunnel syndrome results from inflammation of the median nerve where it passes through an aperture bounded by the bones of the wrist (carpal bones) and the flexor retinaculum muscle, this aperture being commonly referred to as the carpal tunnel. The median nerve supplies sensation to the wrist area as well as the thumb, the index finger, the middle finger and the ring finger. Therefore, when the median nerve becomes irritated and inflamed in the carpal tunnel area, the aforementioned sensations are felt in these areas of the hand and wrist.

Median nerve inflammation that causes carpal tunnel syndrome can be the result of repetitive flexations of the wrist. These repetitive movements are required in numerous activities such as typing or operating a sewing machine. A known solution to the development of carpal tunnel syndrome is the limitation of the flexibility of the wrist. The repetitive flexations that can cause carpal tunnel syndrome are thereby lessened and the median nerve is less likely to become inflamed.

Most wrist supports for prevention of carpal tunnel syndrome consist of a wrist support which may be secured about a person's wrist. Typically, such wrist supports consist of strips of material which, when wrapped about a person's wrist, support the wrist and limit its flexibility.

However, the wrist supports sometimes cover an insufficient area about the wrist to properly limit flexation of the wrist. Or, when in place, the wrist supports constrict use of the fingers and are therefore unusable for many activities that may cause carpal tunnel syndrome. Additionally, the known wrist supports typically provide the same amount of support to the wrist and areas adjacent the wrist. This configurational limitation does not allow greater support directly around the wrist while allowing less support to the areas adjacent the wrist to allow for greater manual dexterity of the hand and fingers. Furthermore, such wrist supports are typically constructed from materials that do not have the desired characteristic of providing impact resistance to the hand and wrist.

To this end, a need has long existed for a wrist support that properly limits the flexation of the wrist and provides varied levels of support to the wrist area, giving more support to areas of the wrist where greater support is required. Also, such a wrist support should provide impact resistance to the wrist and hand while allowing substantially unrestricted movement of the fingers.

BRIEF DESCRIPTION OF THE DRAWINGS

FIG. 3 is a plan view of one side of the wrist support of the present invention.

FIG. 4 is a plan view of a side of the wrist support of the present invention opposite that shown in FIG. 3.

FIG. 5 is a perspective view of the wrist support of the present invention showing placement of a wrist on the wrist support prior to securing the wrist support about the wrist and a portion of the hand.

FIG. 6 is a perspective view of the wrist support of the present invention showing a body member of the wrist support secured around the wrist and a portion of the hand.

DESCRIPTION OF THE PREFERRED EMBODIMENT

Figure 1:
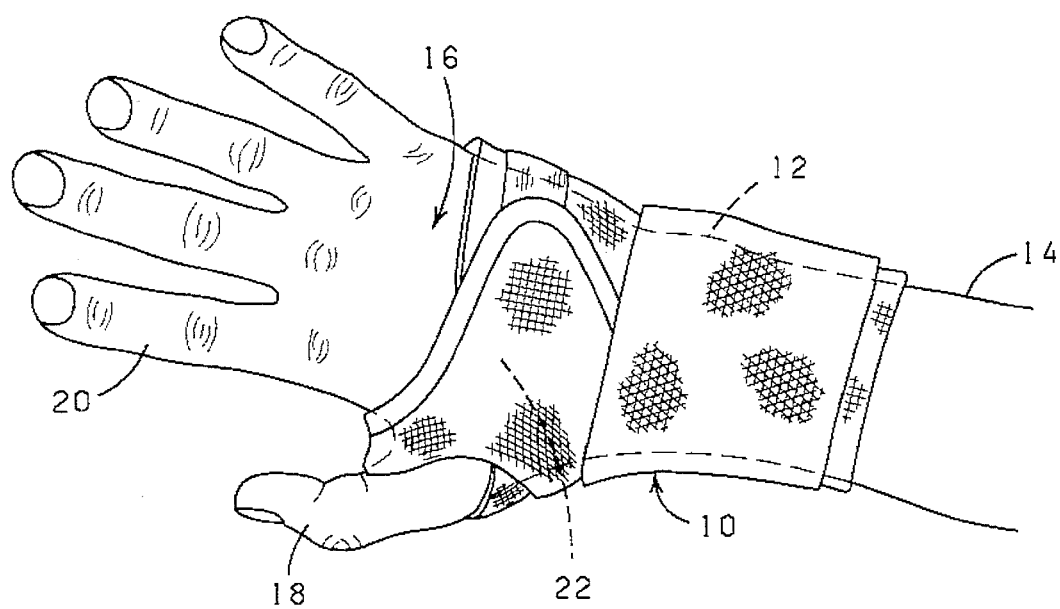
FIG. 1 is a pictorial representation of a back portion of a person's hand and wrist having a wrist support of the present invention positioned thereon.
Figure 2:
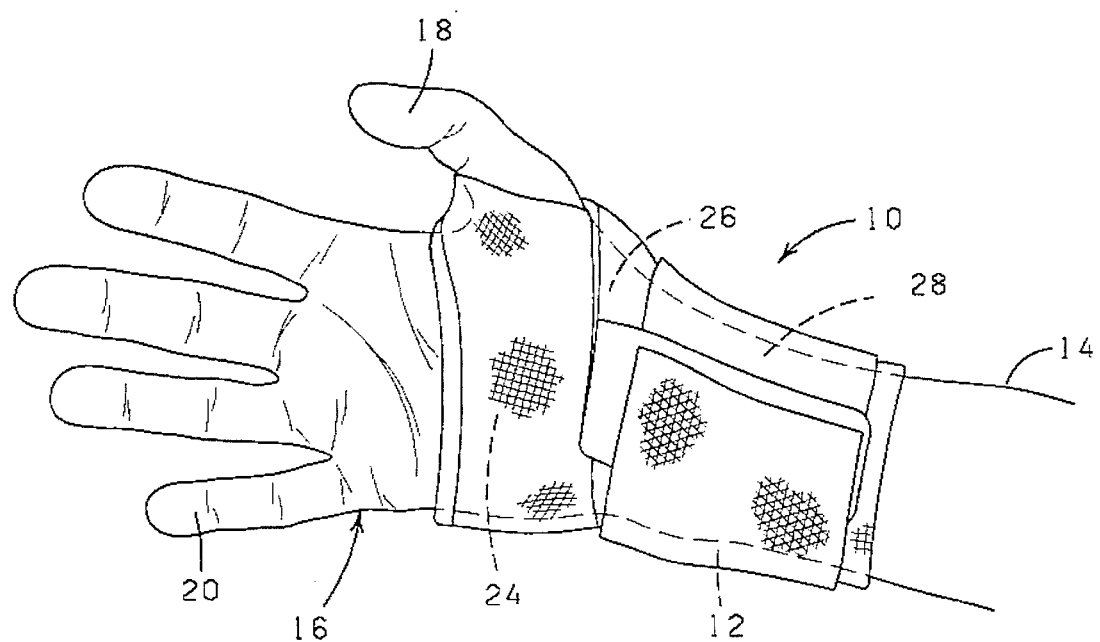
FIG. 2 is a pictorial representation of a front or palm portion of a person's hand and wrist having the wrist support of the present invention positioned thereon.

Shown in FIGS. 1 and 2 is a wrist support constructed in accordance with the present invention and generally designated by the reference numeral 10. The wrist support 10 is positionable about at least a portion of a person's wrist 12, arm 14 and hand 16. As shown in FIG. 1, the hand 16 has a thumb 18, a plurality of fingers (only one of which is designated 20), and a back portion 22 extending from the fingers 20 to the wrist 12. The hand is also characterized as having a palm 24 (FIG. 2) with a heel portion 26. FIG. 2 also shows a front portion 28 of the wrist 12. Although the wrist support 10 is depicted for use on a right hand of a person, it should be noted that the wrist support 10 may be constructed so that it may be used on the left hand.

As more clearly shown in FIGS. 3 and 4, the wrist support 10 is provided with a body member 30, an elongated strap 32 and a flexible support plate 34. The body member 30 includes an upper portion 36 and a lower portion 38, the upper portion 36 having a first end portion 40 and a second end portion 42 and the lower portion 38 having a first end portion 44 and a second end portion 46. The body member 30 also has an upper side 48, a lower side 50, a thumb receiving opening 52 extending through the first end portion 40 of the upper portion 36 of the body member 30, an outer surface 54 (FIG. 3) and an inner surface 56 (FIG. 4). The lower portion 38 of the body member 30 has a width 58 and includes a first section 60 located substantially adjacent the upper portion 36 of the body member 30, a second section 62 located substantially adjacent the lower side 50 of the body member 30, and a third section 64 located between the first section 60 of the lower portion 38 of the body member 30 and the second section 62 of the lower portion 38 of the body member 30. The significance of the construction of the lower portion 38 of the body member 30 will be explained in detail hereinafter.

In order to enhance positioning of the wrist support 10 about the wrist 12, it is desirable to provide the wrist support 10 with a body portion connecting assembly 66 for connecting the first end portion 44 of the lower portion 38 of the body member 30 to the second end portion 46 of the lower portion 38 of the body member 30. The body portion connecting assembly 66 of the wrist support 10 includes a first connector member 67 and a second connector member 68. The first connector member 67 of the body portion connecting assembly 66 is secured to the first end portion 44 of the lower portion 38 of the body member 30 by any suitable means such as sewing, use of an adhesive or the like. The second connector member 68 of the body portion connecting assembly 66 is secured to the second end portion 46 of the lower portion 38 of the body member 30 by any suitable means such as sewing, use of an adhesive or the like. When the wrist support 10 is disposed about the wrist 12, the first connector member 67 of the body portion connecting assembly 66 overlaps the second connector member 68 of the body portion connecting assembly 66 to thereby enable one to connect the first connector member 67 of the body portion connecting assembly 66 to the second connector member 68 of the body portion connecting assembly 66 to hold the body member 30 in place about the wrist 12.

Although the first connector member 67 of the body portion connecting assembly 66 is shown as being secured to the inner surface 56 of the lower portion 38 of the body member 30 and the second connector member 68 of the body portion connecting assembly 66 is shown as being secured to the outer surface 54 of the lower portion 38 of the body member 30, it should be noted that the first connector member 67 of the body portion connecting assembly 66 may be secured to the outer surface 54 of the lower portion 38 of the body member 30 and the second connector member 68 of the body portion connecting assembly 66 may be secured to the inner surface 56 of the lower portion 38 of the body member 30.

The first connector member 67 of the body portion connecting assembly 66 and the second connector member 68 of the body portion connecting assembly 66 are constructed of complementary hook and loop sections which fasten together under hand pressure and which can be quickly and easily separated. The first connector member 67 of the body portion connecting assembly 66 and the second connector member 68 of the body portion connecting assembly 66 may be either the hook section or the loop section. However, one of the first connector member 67 or the second connector member 68 of the body portion connecting assembly 66 must be the hook section and the other of the first connector member 67 or the second connector member 68 of the body portion connecting assembly must be the loop section. An example of such hook and loop sections is Velcro®, a registered trademark for opposing sections of small complementary hooks and loops, available through Velcro Industries, B. V., HOEKENRODE 6, 1102 BR Amsterdam, Netherlands.

Although the first connector member 67 of the body portion connecting assembly 66 and the second connector member 68 of the body portion connecting assembly 66 are shown as being hook and loop sections, it should be understood that any means known in the art for releasably connecting the first end portion 44 of the lower portion 38 of the body member 30 to the second end portion 46 of the lower portion 38 of the body member 30 may be utilized without departing from the scope and spirit of the present invention. For example, the body portion connecting assembly 66 may constitute a strap and buckle, or one or more snap fasteners, etc.

When the wrist support 10 is positioned about the wrist 12, the lower portion 38 of the body member 30 extends from about the heel portion 26 of the palm 24 and over the arm 14 to substantially cover the wrist 12 substantially as shown in FIGS. 5–8. The width 58 of the lower portion 38 of the body member 30 can vary and will be dependent to a large degree on the size of the hand 16 and the wrist 12 of the user. However, in most instances, the width of the lower portion 38 of the body member 30 will range from about 4 inches to about 6 inches.

The first section 60, second section 62 and third section 64 of the lower portion 38 of the body member 30 are constructed from a elastomeric polymeric material. Generally, the third section 64 of the lower portion 38 of the body member 30 provides approximately ½ the width 58 of the lower portion 38 of the body member 30 and the first section 60 and the second section 62 of the lower portion 38 of the body member 30 each provides approximately ¼ of the width 58 of the lower portion 38 of the body member 30, though these ratios may vary if desired.

To provide more support directly around the wrist 12 where it is needed most and to provide a lesser degree of support around the hand 16 and arm 14 to provide for more comfort, a differing degree of stretch is provided for each of the first section 60, second section 62 and third section 64 of the lower portion 38 of the body member 30. It is desirable that the third section 64 of the lower portion 38 of the body member 30 have a lower degree of stretch than the first section 60 or the second section 62 of the lower portion 38 of the body member 30 since the third section 64 of the lower portion 38 of the body member 30 provides support directly around the wrist 12. It is acceptable, however, that the first section 60 and the second section 62 of the lower portion 38 of the body member 30 have the same degree of stretch.

The term "lower degree of stretch" as used herein is understood to mean that, for a given amount of stretching force applied to the material, the material will not stretch as much as a material having a higher degree of stretch. A material having a low degree of stretch is more firm than a material having a high degree of stretch and, therefore, will provide a greater amount of support when wrapped around the wrist 12.

The lower portion 38 of the body member 30 may be constructed of any suitable material that provides the aforementioned characteristics. However, knitted elastic of varying gauge has proven to be most acceptable for construction of the lower portion 38 of the body member 30. For example, one acceptable manner of construction of the lower portion 38 of the body member 30 would be to form the first section 60 and the second section 62 of the lower portion 38 of the body member from 34 gauge knitted elastic while forming the third section 64 of the lower portion 38 of the body member 30 from 26 gauge knitted elastic. (It should be noted that the degree of stretch of the knitted elastic is directly proportional to the magnitude of the gauge.)

To add additional support under the wrist 12 while allowing the wrist 12 to remain at least partially flexible, the flexible support plate 34 is connected to the lower portion 38 of the body member 30. The flexible support plate 34 is attached to the lower portion 38 of the body member 30 so that the flexible support plate 34 is disposed in a substantially covering position over the front portion 28 of the wrist 12 when the wrist support 10 is in place about the wrist 12. The flexible support plate 34 has a length 70 and a width 72 (FIG. 4). The length 70 of the flexible support plate 34 substantially approximates the width 58 of the lower portion 38 of the body member 30. Typically, the length 70 of the flexible support plate 34 ranges from about 3 inches to about 6 inches.

The width of the flexible support plate 34 substantially approximates a width (not shown) of the wrist 12. Typically, the width 72 of the flexible support plate 34 ranges from about 1 inch to about 3 inches.

As shown in FIGS. 3 and 4, the flexible support plate 34 is attached to the lower portion 38 of the body member 30 so as to be disposed adjacent the inner surface 56 of the lower portion 38 of the body member 30. However, it should be understood that the flexible support plate 34 may also be attached to the inner surface 56 or to the outer surface 54 of the lower portion 38 of the body member 30 by any method known in the art, as long as the flexible support plate 34 is disposed in a position where it may function in the manner shown and described herein.

It is preferable that the flexible support plate 34 has sufficient rigidity to prevent damage that occurs from certain repetitive wrist flexations that may cause carpal tunnel syndrome while still maintaining sufficient flexibility to allow the user to perform activities requiring manual dexterity of the hand 16, fingers 20 and thumb 18. To this end, it is desirable that the flexible support plate 34 be sufficiently rigid to limit the flex along the length 70 thereof from about to ±20° to about ±30°. The flexible support plate 34 must also be resilient so as to substantially maintain its original flat shape when no pressure is applied thereto.

The flexible support plate 34 may be constructed of any material provided that the material perform in the manner described hereinbefore. For example, the flexible support plate 34 may be constructed from metal, leather or a polymeric material. However, it is desirable that the flexible support plate 34 be constructed from a polymeric material since a polymeric material will provide sufficient support while providing resiliency so as not to cause permanent deformation of the plate 34.

It is desirable that the lower portion 38 of the body member 30 also include alignment indicia 74 disposed on the inner surface 56 thereof for indicating the position of the flexible support plate 34 to enhance placement of the wrist 12 on the wrist support 10 before securing the wrist support 10 about the wrist 12. The alignment indicia 74 may constitute a line, letter, number, symbol or any other mark that performs the stated function. The alignment indicia 74 may be disposed on the inner surface 56 of the body member 30 in any manner known in the art.

The alignment indicia 74 is disposed on the inner surface 56 of the body member 30 over the location of the flexible support plate 34 a distance 75 from an upper side 76 of the flexible support plate 34, said distance 75 being approximately ¼ of the length 70 of the flexible support plate 34. It should be noted that if the flexible support plate 34 is attached directly to the inner surface 56 of the body member 30, then the alignment indicia 74 will be disposed directly on the flexible support plate 34.

The elongated strap 32 is provided with a first end 78, a second end 80, an inner surface 82 (FIG. 4), an outer surface 84 (FIG. 3), a width 86 and a length 88. The second end 80 of the elongated strap 32 is connected to the lower portion 38 of the body member 30 so that the first end 78 of the elongated strap 32 extends outwardly from the first end portion 44 of the lower portion 38 of the body member 30 and the elongated strap 32 is substantially aligned with the lower portion 38 of the body member 30 substantially as shown in FIGS. 3 and 4.

Although the second end 80 of the elongated strap 32 is shown secured to the lower portion 38 of the body member 30 adjacent the flexible support plate 34, it should be understood that the second end 80 of the elongated strap 32 may be secured anywhere on the outer surface 54 of the lower portion 38 of the body member 30 as long as the elongated strap 32 is capable of functioning in the manner described hereinafter.

The elongated strap 32 is wrappable about the body member 30 so that the inner surface 82 of the elongated strap 32 is adjacently disposed to the outer surface 54 of the body member 30 when the elongated strap 32 is in a wrapped condition about the body member 30.

The elongated strap 32 is constructed from a material which is stretchable between a stretched condition and a non-stretched condition. The tension of the elongated strap 32 may thereby be adjusted to an optimum level of support and comfort when the elongated strap 32 is wrapped about the body member 30 of the wrist support 10.

Preferably, the elongated strap 32 is constructed from knitted elastic. However, it should be noted that the elongated strap 32 may be constructed from any suitable material that provides the desired stretching characteristic. Though the width 86 of the elongated strap 32 may vary depending on the size of the wrist 12, the width 86 of the elongated strap 32 will typically be from about 2 inches to about 4 inches.

The length 88 of the elongated strap 32, when the elongated strap 32 is in either the stretched or the non-stretched condition, is sufficient to encircle the body member 30 of the wrist support 10 when the body member 30 is disposed about the wrist 12. It is desirable that the length 88 of the elongated strap 32 is such that the elongated strap 32 must be placed in the stretched condition in order for the elongated strap 32 to substantially encircle the body member 30 when the wrist support 10 is in place about the wrist 12. When the elongated strap 32 is disposed about the body member 30 in the stretched condition, more support is given to the wrist 12 by the wrist support 10.

The wrist support 10 is provided with a strap connecting assembly 90 for connecting the first end 78 of the elongated strap 32 to the lower portion 38 of the body member 30. The strap connecting assembly 90 of the wrist support 10 includes a first connector member 91 and a second connector member 92. The first connector member 91 of the strap connecting assembly 90 of the wrist support 10 is secured to the first end 78 of the elongated strap 32 (FIG. 4) and is releasably connectable to the second connector member 92 of the strap connecting assembly 90 of the wrist support 10.

As shown in FIGS. 3 and 4, the second connector member 92 of the strap connecting assembly 90 is attached to the outer surface 54 of the lower portion 38 of the body member 30. The second end 80 of the elongated strap 32 is attached adjacent the second connector member 92 of the strap connecting assembly 90 and the first end 78 of the elongated strap 32 extends therefrom so that the elongated strap 32 encircles the body member 30 about one time when the wrist support 10 is in place about the wrist 12 and the first connector member 91 of the strap connecting assembly 90 is connected to the second connector member 92 of the strap connecting assembly 90.

Although the second connector member 92 of the strap connecting assembly 90 is shown attached to the outer surface 54 of the lower portion 38 of the body member 30, it should be understood that the second connector member 92 of the strap connecting assembly 90 may instead be attached to the outer surface 84 of the elongated strap 32 if it is desired that the elongated strap 32 be wrapped about the body member 30 more than one time before the elongated strap 32 is fastened to the body member 30.

The first connector member 91 of the strap connecting assembly 90 and the second connector member 92 of the strap connecting assembly 90 are constructed of complementary hook and loop sections which fasten together under hand pressure and which can be quickly and easily separated. The first connector member 91 of the strap connecting assembly 90 and the second connector member 92 of the strap connecting assembly 90 may be either the hook section or the loop section. However, either the first connector member 91 of the strap connecting assembly 90 or the second connector member 92 of the strap connecting assembly 90 must be the hook section and the other of the first connector member 91 of the strap connecting assembly 90 or the second connector member 92 of the strap connecting assembly 90 must be the loop section. An example of such hook and loop sections is Velcro®, a registered trademark for opposing sections of small complementary hooks and loops, available through Velcro Industries, B. V., HOEKENRODE 6, 1102 BR Amsterdam, Netherlands.

Although the first connector member 91 of the strap connecting assembly 90 and the second connector member 92 of the strap connecting assembly 90 are shown as being hook and loop sections, it should be understood that any means known in the art for releasably connecting the first end 78 of the elongated strap 32 to the lower portion 38 of the body member 30 may be utilized without departing from the scope and spirit of the present invention. For example, the strap connecting assembly 90 may constitute a strap and buckle, or one or more snap fasteners, etc.

The first end portion 40 of the upper portion 36 of the body member 30 defines a flap 94. The flap 94 is disposed in a covering position over a portion of the first end portion 44 of the lower portion 38 of the body member 30 substantially as shown. The thumb receiving opening 52 is formed through the flap 94 defined by the upper portion 36 of the body member 30.

The wrist support 10 further includes an adjusting tab 96 attached to the upper side 48 of the body member 30. The adjusting tab is provided with a first end 98, a second end 100, a first side 102 and a second side 104. The first end 98 of the adjusting tab 96 is attached to flap 94 of the body member 30 so that the second end 100 of the adjusting tab 96 extends outwardly therefrom.

The wrist support 10 is provided with a tab connecting assembly 106 for connecting the adjusting tab 96 to the outer surface upper portion 36 of the body member 30. The tab connecting assembly 106 includes a first connector member 108 and a second connector member 110. It is preferable that at least a portion of the first side 102 of the adjusting tab 96 be provided with a hook section of connecting material to provide the first connector member 108, and at least a portion of the outer surface 54 of upper portion 36 of the body member 30 be provided with a complementary loop section of the connecting material to provide the second connector member 110 so that the adjusting tab 96 may be releasably and adjustably connected to the second end portion 42 of the upper portion 36 of the body member 30 so that the body member 30 extends about the wrist 12, across the back portion 22 of the hand 16 adjacent the wrist 12 and from the thumb 18 to the heel portion 26 of the palm 24. The upper portion 36 of the body member 30 may thereby be tightened around the palm 24 of the hand 16 to provide multiple directed forces on the hand 16 and wrist 12 so as to maintain the wrist 12 in a substantially neutral position.

It is desirable that the loop section of the outer surface 54 of the body member 30, which functions as the second connecting member 110 cover a relatively large area of the outer surface 54 of the body member 30 so the user will have wide discretion as to where to place the adjusting tab 96. The first connector member 108 of the tab connecting assembly 106 and the second connector member 110 of the tab connecting assembly 106 may be either the hook section or the loop section of the connecting material. However, either the first connector member 108 of the strap connecting assembly 106 or the second connector member 110 of the strap connecting assembly 106 must be the hook section and the other of the first connector member 108 of the tab connecting assembly 106 or the second connector member 110 of the tab connecting assembly 106 must be the loop section. An example of such hook and loop sections is Velcro®, a registered trademark for opposing sections of small complementary hooks and loops, available through Velcro Industries, B. V., HOEKENRODE 6, 1102 BR Amsterdam, Netherlands.

Although the first connector member 108 of the tab connecting assembly 106 and the second connector member 110 of the tab connecting assembly 106 are shown as being hook and loop sections, it should be understood that any means known in the art for releasably connecting the first end 98 of the tab connecting assembly 106 to the second end portion 42 of the upper portion 36 of the body member 30 may be utilized without departing from the scope and spirit of the present invention. For example, the tab connecting assembly 106 may constitute a strap and buckle, or one or more snap fasteners, etc.

The upper portion 36 of the body member 30 is constructed from a stretchable material capable of supporting the wrist 12 and hand 16 when the wrist support 10 is in place about the wrist 12. Preferably, the upper portion 36 of the body member 30 is constructed from a stretchable material which also provides impact protection to the area covered by the upper portion 36 of the body member 30. It should be noted that the upper portion 36 of the body member 30 may be a combination of materials that provide these characteristics.

In the preferred embodiment, the upper portion 36 of the body member 30 is constructed of neoprene to provide support and impact resistance. The thickness of the neoprene ranges from about 1/32 inch to about 5/32 inch. The inner surface 56 of the body member 30 is covered with a terry material over the upper portion 36 of the body member 30 to provide greater comfort for the user. The second connector member 110 comprises a loop material extending over the outer surface 54 so as to connectably receive the adjusting tab 96 anywhere on the outer surface 54 of the body member 30 on the upper portion 36 of the body member 30.

FIGS. 5–8 depict the manner in which the wrist support 10 is placed about the wrist 12. The wrist support 10 is laid flat with the inner surface 56 of the body member 30 facing the user substantially as shown (FIG. 5). The user places the thumb 18 through the thumb receiving opening 52 formed in the upper portion 36 of the body member 30 and places the wrist 12 on the inner surface 56 of the body member 30 so that the wrist 12 is substantially disposed over the alignment indicia 74 located on the inner surface 56 of the body member 30.

The lower portion 38 of the body member 30 is then wrapped about the wrist 12 until the first connector member 67 of the body portion connecting assembly 66 overlies the second connector member 68 of the body portion connecting assembly 66. The first connector member 67 of the body portion connecting assembly 66 is pressed onto the second connector member 68 of the body portion connecting assembly 66 so as to releasably connect the first end portion 44 of the lower portion 38 of the body member 30 to the second end portion 46 of the lower portion 38 of the body member 30. The tension of the lower portion 38 of the body member 30 may be adjusted by the user for comfort and support by adjusting the placement of the first connector member 67 of the body portion connecting assembly 66 on the second connector member 68 of the body portion connecting assembly 66.

Figure 7:
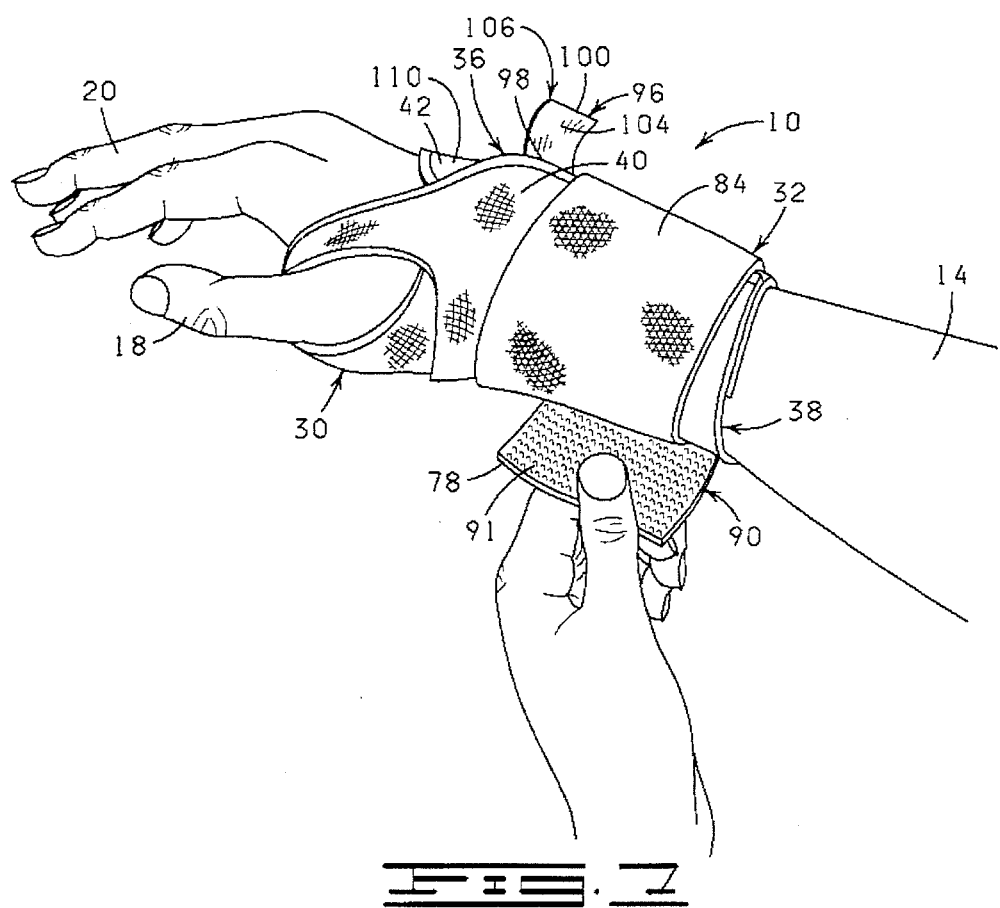
FIG. 7 is a perspective view of the wrist support of the present invention showing an elongated strap of the wrist support secured around the wrist.

The elongated strap 32 is then wrapped about the lower portion 38 of the body member 30, substantially as shown in FIG. 7, by stretching the elongated strap 32 around the lower portion 38 of the body member 30 so that the first connector member 91 of the strap connecting assembly 90 overlies the second connector member 92 of the strap connecting assembly 90. The first connector member 91 of the strap connecting assembly 90 is pressed onto the second connector member 92 (FIG. 3) of the strap connecting assembly 90 to releasably connect the first end 78 of the elongated strap 32 to the wrist support 10. As with the lower portion 38 of the body member 30, the tension of the elongated strap 32 may be adjusted for comfort and support by adjusting the placement of the first connector member 91 of the strap connecting assembly 90 on the second connector member 92 of the strap connecting assembly 90.

Figure 8:
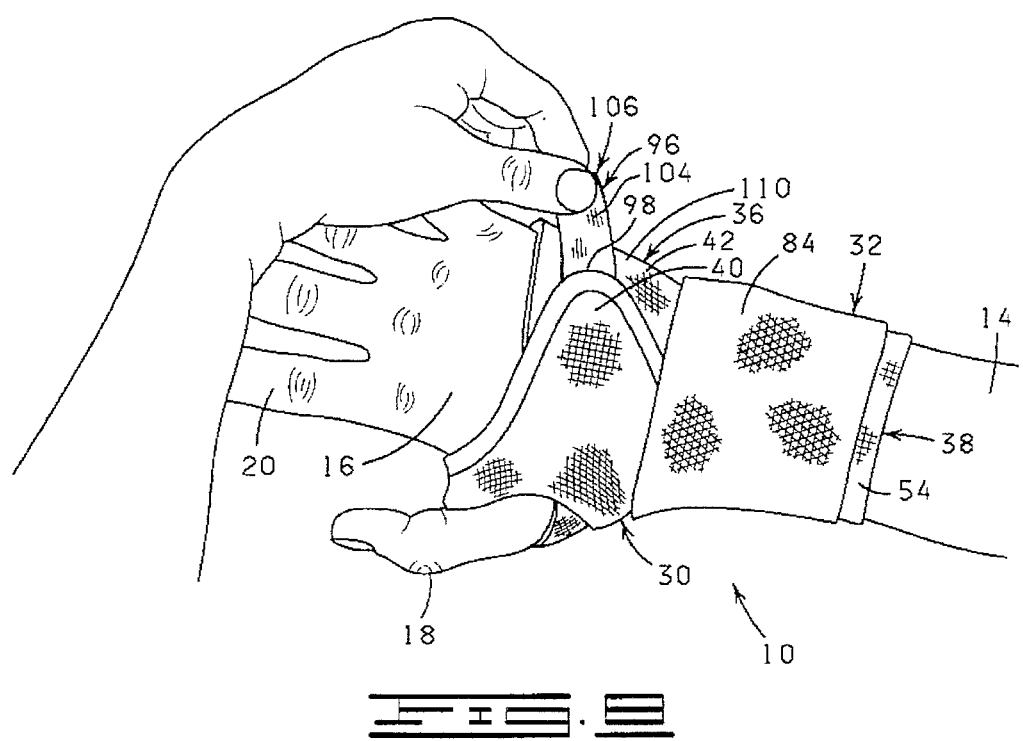
FIG. 8 is a perspective view of the wrist support of the present invention showing an upper portion of the body member of the wrist support being secured around the wrist, hand and thumb.

After the lower portion 38 of the body member 30 and the elongated strap 32 have been placed about the wrist 12, the upper portion 36 of the body member 30 is releasably secured in place substantially as shown in FIG. 8. The user grasps and pulls the adjusting tab 96 to the proper tension for the desired support for the wrist 12 and comfort for the user. The user then places the adjusting tab 96 over the second end portion 42 of the upper portion 36 of the body member 30. The user presses the first connector member 108 (FIG. 4) on the first side 102 of the adjusting tab 96 onto the second connector member 110 located on the outer surface 54 of the body member 30 to releasably connect the adjusting tab 96 to the wrist support 10. The tension of the upper portion 36 of the body member 30 may then be readjusted for the desired support and comfort if necessary. The wrist support 10 is now properly in place about the user's wrist 12.

Changes may be made in the embodiment of the invention described herein or in parts or elements of the embodiment described herein without departing from the spirit and/or scope of the invention as defined in the following claims.

What is claimed is:

1. A wrist support positionable about a hand and wrist of an individual to provide support to the wrist, the wrist characterized as having a front portion and the hand characterized as having a thumb, a plurality of fingers, a back portion extending from the fingers to the wrist and a palm having a heel portion, the wrist support comprising:

a body member having an upper portion and a lower portion, the lower portion of the body member extendable about the wrist, the upper portion having a first end portion and a second end portion, the second end portion of the upper portion of the body member extendable from the back of the hand, across the palm of the hand and to the thumb, the first end portion of the upper portion connected to the lower portion of the body member so as to form a thumb receiving opening and a flap, the flap positionable across a portion of the back of the hand and over a portion of the lower portion of the body member and a portion of the second end of the upper portion of the body member;

flap connecting means for adjustably connecting the flap to the second end portion of the upper portion of the body member when the body member is extended about the wrist and the thumb is positioned in the thumb receiving opening such that the flap extends across a portion of the back of the hand and overlaps the lower portion of the body member and the second end portion of the upper portion of the body member;

a strap having a first end and a second end, the second end connected to the lower portion of the body member and the strap having a length sufficient for the strap to be encircled about the lower portion of the body member when the body member is positioned about the wrist;

strap connecting means for adjustably connecting the first end of the strap to the body member upon wrapping the strap about the lower portion of the body member; and a flexible support plate connected to the body member so that when the body member is positioned about the wrist and hand, the support plate is disposed along the front portion of the wrist, wherein the body member, the strap, and the support plate cooperate to maintain the wrist in a neutral position while allowing full movement of the fingers and thumb.

2. The wrist support of claim 1 wherein the upper portion of the body member is fabricated of neoprene.

3. The wrist support of claim 1 wherein the individual is further characterized as having a forearm, and wherein the lower portion of the body member is fabricated of a variable stretch elastic material defining a first section, a second section and a third section, the first section located on the lower portion of the body member so as to be positionable about the hand when the body member is positioned about the hand and the wrist, the second section located on the lower portion of the body member so as to be positionable about the forearm when the body member is positioned about the hand and the wrist, and the third section located between the first section and the second section so as to be positionable about the wrist when the body member is positioned about the hand and wrist, the third section having a lower degree of stretch relative to the first and second sections effecting increased support to the wrist while providing increased comfort to the hand and forearm.

* * * * *